(12) United States Patent
Bhattacharjee et al.

(10) Patent No.: US 11,432,744 B2
(45) Date of Patent: Sep. 6, 2022

(54) LUNG CONDITION MONITORING DEVICE (71) Applicant: INDIAN INSTITUTE OF TECHNOLOGY, GUWAHATI, Guwahati (IN)

(72) Inventors: Mitradip Bhattacharjee, Guwahati (IN); Dipankar Bandyopadhyay, Guwahati (IN); Harshal B. Nemade, Guwahati (IN)

(73) Assignee: INDIAN INSTITUTE OF TECHNOLOGY, GUWAHATI, Guwahati (IN)

(*) Notice: Subject to any disclaimer, the term of this patent is extended or adjusted under 35 U.S.C. 154(b) by 715 days.

(21) Appl. No.: 16/080,021

(22) PCT Filed: Aug. 29, 2017

(86) PCT No.: PCT/IN2017/050363
§ 371 (c)(1),
(2) Date: Aug. 27, 2018

(87) PCT Pub. No.: WO2018/061022
PCT Pub. Date: Apr. 5, 2018

(65) Prior Publication Data
US 2020/0163587 A1    May 28, 2020

(30) Foreign Application Priority Data

Sep. 28, 2016   (IN) .............................. 201631033190

(51) Int. Cl.
*A61B 5/087* (2006.01)
*A61B 5/085* (2006.01)
(52) U.S. Cl.
CPC ............ *A61B 5/0871* (2013.01); *A61B 5/085* (2013.01); *A61B 2562/029* (2013.01); *A61B 2562/0271* (2013.01)

(58) Field of Classification Search
CPC ................. A61B 5/0871; A61B 5/085; A61B 2562/0271; A61B 2562/029; A61B 5/097;
(Continued)

(56) References Cited

U.S. PATENT DOCUMENTS 3,726,271 A   4/1973 Mondshine
4,282,883 A   8/1981 Yerushalmy
(Continued)

FOREIGN PATENT DOCUMENTS

DE   102007033906 A1   1/2009
EP       0437055 A1   7/1991
(Continued)

OTHER PUBLICATIONS

Mogera et al. (Ultrafast response humidity sensor using supramolecular nanofibre and its application in monitoring breath humidity and flow, Scientific Reports, pp. 1-9, Feb. 2014 (Year: 2014).*
(Continued)

*Primary Examiner* — Jacqueline Cheng
*Assistant Examiner* — Tho Q Tran
(74) *Attorney, Agent, or Firm* — Pearl Cohen Zedek Latzer Baratz LLP (57) ABSTRACT

The present invention discloses a Lung condition monitoring device for performing ultrafast detection of humidity level in exhaled air while breathing out and therefrom detect condition of the human lungs in real time. The Lung 5 condition monitoring device comprises a mouthpiece for forcibly exhaling air there through, one or more humidity sensor to measure the variable electrical resistance based on level of adsorption of water molecules thereon of the humidity content of exhaled air and real time monitoring unit operatively connected to said humidity sensor and having correlating means for correlating 10 the change in humidity level and related variation in the electrical resistance due to
(Continued)

exhalation to peak flow rate of the exhaled air for monitoring lung condition. The Lung condition monitoring device is also capable of wireless data transfer to any peripheral computing device such as mobile phone via wireless connectivity and show the test results on the mobile phone display with the help of a 15 proprietary application embodied in the phones operating system. The mobile interface increases the portability, data monitoring, and user friendliness of the device. Further, the mobile interface helps in storage and analysis of big time data for prognosis, diagnosis, and therapeutic purposes.

15 Claims, 10 Drawing Sheets

(58) Field of Classification Search
CPC ...... A61B 5/082; A61B 5/087; G01N 27/121; G01N 27/126; G01N 33/497
See application file for complete search history.

(56) References Cited

U.S. PATENT DOCUMENTS

| | | | |
|---|---|---|---|
| 4,298,347 A | 11/1981 | Walsh | |
| 4,704,029 A | 11/1987 | Van Heuvelen | |
| 4,799,491 A | 1/1989 | Eckerle | |
| 4,869,261 A | 9/1989 | Penaz | |
| 5,224,487 A | 7/1993 | Bellofatto et al. | |
| 5,277,195 A | 1/1994 | Williams | |
| 5,522,397 A | 6/1996 | Vermaak | |
| 5,565,630 A | 10/1996 | Shene | |
| 5,613,497 A | 3/1997 | Debush | |
| 5,627,324 A | 5/1997 | Shene | |
| 5,634,471 A | 6/1997 | Fairfax et al. | |
| 5,816,246 A | 10/1998 | Mirza | |
| 5,944,670 A | 8/1999 | Katzman | |
| 6,090,049 A | 7/2000 | Cha | |
| 6,110,522 A | 8/2000 | Lepper, Jr. et al. | |
| 6,238,353 B1 | 5/2001 | Weinstein et al. | |
| 6,443,906 B1 | 9/2002 | Ting et al. | |
| RE38,728 E | 4/2005 | Katzman et al. | |
| 6,889,564 B1 | 5/2005 | Marcotte et al. | |
| 6,890,305 B2 | 5/2005 | Irie et al. | |
| 7,063,669 B2 | 6/2006 | Brawner et al. | |
| 7,094,208 B2 | 8/2006 | Williams et al. | |
| 7,153,272 B2 | 12/2006 | Talton | |
| 7,390,305 B2 | 6/2008 | Nuttall | |
| 7,635,339 B2 | 12/2009 | Harnoncourt et al. | |
| 8,034,002 B2 | 10/2011 | Coifman | |
| 8,246,550 B2 | 8/2012 | Morris | |
| 8,398,546 B2 | 3/2013 | Pacione et al. | |
| 10,893,825 B2 * | 1/2021 | Dieffenderfer | A61B 5/6898 |
| 2003/0171687 A1 | 9/2003 | Irie et al. | |
| 2004/0204466 A1 | 10/2004 | Agarwal et al. | |
| 2005/0085740 A1 | 4/2005 | Davis et al. | |
| 2010/0031964 A1 | 2/2010 | Turek et al. | |
| 2011/0054359 A1 | 3/2011 | Sazonov et al. | |
| 2013/0317379 A1 | 11/2013 | Brimer et al. | |
| 2014/0350367 A1 | 11/2014 | Subramaniam | |

FOREIGN PATENT DOCUMENTS

| | | |
|---|---|---|
| EP | 0573060 A2 | 12/1993 |
| EP | 1271384 A1 | 1/2003 |
| WO | WO 2001/097887 | 12/2001 |
| WO | WO 2015/117046 | 8/2015 |

OTHER PUBLICATIONS

"Electrical Characterization of CdS Nanoparticles for Humidity Sensing Applications", Ramazan Demir, Salih Okur, and Mavi e eker, Industrial & Engineering Chemistry Research 2012, 51 (8), 3309-3313.

"Detection of lung, breast, colorectal, and prostate cancers from exhaled breath using a single array of nanosensors", G Peng, M Hakim, Y Y Broza, S Billan, R Abdah-Bortnyak, A Kuten, U Tisch & H Haick, British Journal of Cancer (2010) 103, 542-551, Aug. 10, 2010.

International Search Report of PCT Application No. PCT/IN2017/050363 dated Nov. 28, 2017.

* cited by examiner

LUNG CONDITION MONITORING DEVICE

CROSS-REFERENCE TO RELATED APPLICATIONS

This application is a National Phase Application of PCT International Application No. PCT/IN2017/050363, International Filing Date Aug. 29, 2017, entitled "A LUNG CONDITION MONITORING DEVICE", published on Apr. 5, 2018, under publication No. WO 2018/061022, which claims priority of Indian Patent Application No. 201631033190, filed on Sep. 28, 2016, all of which are hereby incorporated by reference in their entireties.

FIELD OF THE INVENTION

The present invention relates to lung function/status/condition monitoring. More specifically, the present invention is directed to develop a Lung condition monitoring device with nanoparticle based humidity sensor configured for performing ultrafast detection of humidity level in the exhaled air of a human while breathing out and there from detect condition of the human lungs in real time. The present Lung condition monitoring device is portable and advantageously adapted to operate as point-of care testing gadgets or devices for checking fitness of the lungs of a person. The present Lung condition monitoring device is also capable of wireless data transfer to a peripheral computing device like smart mobile phone via 'Bluetooth' connectivity for showing test results on the mobile phone display with the help of an application developed for the open standard operating system.

BACKGROUND ART

Frequent monitoring of quality of health has become a part of modern life because it improves the life expectancy by capturing the onset of many complex and irreversible health hazards at very early stages.

In this direction, user-friendly and portable point-of care testing (POCT) gadgets have enabled a large section of mass to evaluate and maintain a minimum quality of fitness of different body parts. For example, a number of commercially available POCT devices have helped the routine monitoring of blood pressure, body-weight, or blood sugar to avoid the health hazards associated with the variations in these fitness indices [Ref: U.S. Pat. Nos. 4,298,347; 4,799, 491; EP0437055A1; U.S. Pat. Nos. 4,704,029A; 6,110, 522A; 4,869,261A; 6,443,906B1; 8,398,546B2; US2011/ 0054359A1].In particular, the aged, children, or the disabled persons have been immensely benefitted by these POCT devices because of their utility in evaluation and stabilization of the severe or critical health conditions before consulting the physicians or experts. Thus, extensive research efforts have been invested over past few decades to develop POCT devices to track multifarious fitness markers.

Although the development of POCT gadgets has been rapid over the past few decades, there are many different fitness markers that immediately need attention. One such fitness marker is the activity of the lung, which is in general measured through different lung function tests [Ref: US2010/0031964A1; U.S. Pat. Nos. 6,890,305B2; 7,635, 339B2]. Lung function tests are important to measure the fitness of the lungs for the asthma, bronchitis, or pneumonia patients, which are rather chronic diseases among the children and elderly persons in most of the developing countries [refer to, Global Alliance Against Chronic Respiratory Diseases, WHO $9^{th}$ General Meeting Report, 14-16 Aug. 2014 in Salvador, Brazil].

Most of the presently available techniques to monitor lung function are available through centralized agencies, pathological testing units, or hospitals [Ref: U.S. Pat. No. 8,246, 550B2]. Further, these methodologies require medical experts for functioning as well as analysis of the performance. However, the availability of simple, user-friendly, and portable lung function kits not only enable the common people to monitor the fitness of the lungs, but also may spread mass-awareness on the fitness of the lungs for a healthier living.

The present methodology to diagnose the chronic obstructive pulmonary diseases (COPD) such as asthma, bronchitis, or pneumonia is complex as well as costly, which requires a comprehensive medical investigation of pulmonary function using spirometry [Ref: U.S. Pat. No. 8,246,550B2]. Reversible airway obstruction is the most common symptom of a patient having COPD [Ref: US2004/0204466A1].

Importantly, since these techniques are only available in the centralized agencies, pathological testing units, or hospitals for a given period of time, in many situations the airway obstructions go unnoticed for a patient at the time of diagnosis. In such situations, a more intensive bronchial challenge test (BCT) is performed to confirm the status of various COPD, in particular asthma [Ref: WO2001/ 097887A1]. In BCT, the patient inhales nebulized methacholine or histamine to provoke broncho-constriction or narrowing of the airways, which is then quantified by spirometry [Ref: U.S. Pat. No. 6,890,305B2]. These processes are not only time consuming, but also significantly painful for the patients because they have to wait for long hours in the queues in the centralized agencies, pathological testing units, or hospitals while having the breathing problems. In addition, most of the bronchial congestion can happen during the odd hours of the day for children or elderly persons and in such situations a reliable, reproducible, stable, portable, and user-friendly device to measure the extent of fitness of the lungs is presently unavailable [Ref: U.S. Pat. No. 5,224,487; EP0573060A2; U.S. Pat. Nos. 5,277,195; 5,522,397; 5,565,630; 5,613,497; 5,627,324; 5,634,471; 5,816,246; 5,944,670; EP1271384A1].

The most commonly employed devices to monitor the lung health are peak flow meter and spirometer [Ref: US2003/0171687A1; U.S. Pat. No. 6,889,564B1; US2005/ 0085740A1; RE38728E; U.S. Pat. Nos. 7,094,208B2; 7,153, 272B2; 7,390,305B2]. The Peak flow meter is an instrument that measures the peak flow rate of forcibly exhaled air from a person's fully inflated lungs. In this device, the maximum flow rate of exhaled air is employed as the parameter to decide the health of the lungs. Different types of peak flow meters are available in the market and a large number of such devices have been patented [Ref: U.S. Pat. Nos. 7,390,305B2; 6,889,564B1; 8,034,002B2]. The peak flow meters can largely categorized into three distinct types, (a) linear or in-line, (b) rotary, and (c) electronic [Ref: U.S. Pat. Nos. 7,390,305B2; 6,889,564B1; 8,034,002B2].

The linear peak flow meter is composed of a cylindrical housing, which has a restrictor near the inlet and an indicator that moves with the force of exhaled air [Ref: U.S. Pat. No. 7,390,305B2]. The air exhaled during forced breathing flows through a cylindrical column and moves out through the outlet. To evaluate the force of exhaled air, which is also an indication of the fitness of the lungs, a piston-spring combination is kept in contact with the restrictor. When a person exhales air at the inlet during the test, the restrictor restricts the air flow and the piston connected to the restrictor is forced to move in the direction of flow. Once the person stops exhaling, the spring takes the piston back to its previous position owing to lack of pressure from the back side, keeping the indicator to the "peak flow" position in the slot. The position of the indicator with the spring actuation is correlated to the flow rate of the forcible breathing.

The rotary peak flow meters are very similar to the linear ones and are composed of a rectangular housing composed of an air inlet, an outlet with a restriction, and a semicircular slot for the indicator [Ref: U.S. Pat. No. 6,889,564B1]. A vane arrangement is attached to a torsion spring, which helps a flag to rotate back to its original position at the stop of the exhalation. Thus far, although the peak flow meters have served the purpose well, the digital gadgets with higher precision, stability, reliability, and repeatability are essential.

The electronic type peak flow meters are battery powered, relatively more accurate and user friendly [Ref: U.S. Pat. No. 8,034,002B2; US2014/0350367A1]. They measure peak flow rate of the forcibly exhaled air with the help of electronic principles. However, because of the high cost of fabrication and manufacturing, these devices are of non-economic and not available as POCT devices for the common people.

Alternatively, spirometers are also employed for basic Pulmonary Function Tests (PFT) to determine the conditions of the COPD [Ref: U.S. Pat. No. 7,063,669B2]. Different varieties of spirometer are also available such as, (a) Plethysmograph—suitable for measuring the components of lung volume [Ref: U.S. Pat. No. 3,726,271A]; (b) Pneumotachometer—measures the flow rate of gases by detecting pressure drop [Ref: U.S. Pat. No. 6,090,049A]; (c) Digital Spirometers—electronically compute air flow rates in absence of moving parts [Ref: U.S. Pat. No. 7,063,669B2]. The other varieties of spirometers employ pressure transducers, ultrasonic, or water gauge to measure the fitness of the lungs [Ref: U.S. Pat. Nos. 4,282,883A; 5,627,324A]. The spirometers are often employed to evaluate different symptoms associated with COPD, such as volume inhaled and exhaled by the lungs, length of breathing, contaminants coming out through breathing, length of obstructive and restrictive ventilation patterns, and effects of medication, among others [Ref: U.S. Pat. Nos. 7,063,669B2; 6,238,353B1; US2013/0317379A1]. Apart from the peak flow meters or spirometers, different other breath testing techniques are also available [Ref: US2003/0171687A1; U.S. Pat. No. 6,889,564B1; US2005/0085740A1; RE38728E; U.S. Pat. Nos. 7,094,208B2; 7,153,272B2; 7,390,305B2; DE102007033906A1], which face the limitations associated with portability or economy or reliability or stability, essential for the development of any futuristic POCT device targeting the detection of state of the illness associated with different COPDs.

It is thus there has been a need for developing a low cost, portable yet accurate Lung monitoring device for checking fitness of the lung of a person which would properly address limitations of the existing lung health testing device.

OBJECT OF THE INVENTION

It is thus the basic object of the present invention is to develop a low cost, portable yet accurate Lung monitoring device which would be adapted to detect condition of the lung in real time and operate as point-of care testing gadgets or devices for checking fitness of the lungs of a person.

Another object of the present invention is to develop a Lung monitoring device which would be adapted to perform basic Pulmonary Function Tests (PFT) to determine the conditions of the COPD and accordingly inform about its user upon detecting the conditions of the COPD.

Yet another object of the present invention is to develop a Lung monitoring device which would be adapted to detect humidity level in exhaled breathing air from the user and correlate the same with peak flow rate of exhalations from lung for determining the lung status or condition.

Another object of the present invention is to develop a Lung monitoring device with rapid recoverable nanoparticle based humidity sensor for performing multiple ultrafast detection of the humidity level in the exhaled breathing air.

Yet another object of the present invention is to develop a Lung monitoring device which would be adapted to communicate with peripheral computing device for recording/updating/analyzing/displaying the detected lung condition.

Yet another object of the present invention is to develop a Lung monitoring device which would be adapted to involve a 'Bluetooth' interface for wireless data exchange connectivity to any commercially available mobile phone device.

Yet another object of the present invention is to develop an open standard application for the mobile phones operating system which can be integrated with the present Lung condition monitoring device with the 'Bluetooth' wireless connectivity to enable monitoring of the lung function conditions on the display panel of the mobile phone through wireless data exchange.

SUMMARY OF THE INVENTION

Thus according to the basic aspect of the present invention there is provided a Lung condition monitoring device comprising mouthpiece for forcibly exhaling air there through;

humidity sensor for variable electrical resistance based on level of adsorption of water molecules thereon of humidity of the exhaled air;

and real time monitoring unit operatively connected to said humidity sensor and having correlating means for correlating the change in humidity level and related variation in the electrical resistance due to exhalation to peak flow rate of the exhaled air for monitoring lung condition.

According to a preferred embodiment of the present invention, the present Lung condition monitoring device comprises heating arrangement having a heating element for rapid desorption of the water molecule from the humidity sensor and recovery of the humidity sensor for subsequent detection of the humidity level.

According to another preferred embodiment of the present invention, the present Lung condition monitoring device comprises said mouthpiece having an open area to receive exhaled breathing air from a user and at its other end operatively connected to said humidity sensor in humidity sensor unit;

said humidity sensor unit exposed to rapid decrease in the electrical resistance of the humidity sensor due to the adsorption of the water molecules from the exhaled breathing air during forced exhalation;

said heating element cooperative with said humidity sensor to increase temperature of the humidity sensor post adsorption of the water molecules for rapid desorption of the water molecule from the humidity sensor and recovery of the humidity sensor for subsequent detection of the humidity level; and said real time monitoring unit to detect lung status and other health parameters by detecting maximum change in the electrical resistance across the humidity sensor and correlating the same with the peak flow rate of exhalations from lung.

According to another aspect in the present Lung condition monitoring device, the humidity sensor unit comprises at least one opening slot to allows the exhaled breathing air to flow in;

one or more holes on sidewall of humidity sensor unit's housing to operate as outlets of the air from the humidity sensor unit; and sensor supporting structure to hold the humidity sensor in the humidity sensor unit.

According to another aspect in the present Lung condition monitoring device, the humidity sensor includes one or more films of porous CdS nanoparticles, each comprising Au nanoparticle embedded thermally conductive paper substrate having thereon the porous CdS nanoparticles constituting a nanoparticle surface for rapid adsorption of the water molecules; and silver electrodes for operatively connecting said nanoparticle surface with the real time monitoring unit.

According to another aspect in the present Lung condition monitoring device, the heating element is placed between the humidity sensors and the sensor supporting structure.

According to another aspect in the present Lung condition monitoring device, the heating element comprises a metallic wire in coil form embedded in a polymer matrix or substrate; and two electrodes for connecting a power source with the coil to operate the heating element and generate heat.

According to another aspect, the present Lung condition monitoring device comprises a thermistor positioned between the sensor supporting structure and the heating element to sense temperature of the heating element and act as a negative feedback to control the temperature.

According to yet another aspect in the present Lung condition monitoring device, the heating element preferably includes copper wire of diameter 180 µm coiled in a 1 cm square area having 80 turns fixed in an adhesive paper substrate to keep the structure intact.

According to a further aspect in the present Lung condition monitoring device, the real time monitoring unit includes a small cabinet preferably made of plastic housing a control assembly and the power source;

plurality of indicator LEDs on housing of the real time monitoring unit for indicating status of the lung;

a power switch operatively connected with the power source to activate/deactivate the device and ON-OFF indicator LED to display activation of the device.

According to yet another aspect in the present Lung condition monitoring device, the control assembly includes a heating element control module comprising a square pulse generator to operate and maintain the heating element's temperature;

a sensor unit control module having a connector which connects the sensor with the indicator LED control module via associated resistive network;

and an indicator LED control module having a resistive network operatively connecting the indicator LEDs with the humidity sensor to activate one or more of the indicator LEDs depending on the status of the lung of the user.

According to another aspect in the present Lung condition monitoring device, the indicator LED control module is configured to activate one or more of the indicator LEDs depending on the change in the electrical resistance of the humidity sensor and correlating the same with the peak flow rate of exhalations from lung;

wherein the peak flow rate of exhalations from the lung is an indicator of degree of obstruction in airways of bronchi and linearly vary with the change in the resistance of the nanoparticle sensor due to the adsorption of the water molecules from the exhaled breathing air during forced exhalation; and wherein higher value of the peak flow rate of exhalations indicates healthy lungs and lower values indicate the diseased state of the lungs.

According to a further aspect in the present Lung condition monitoring device, the indicator LED control module is configured to activate any one or more of three indicator LEDs for indicating status of the lung includes the resistive network adapted to drive current through the LEDs for activating all the LEDs when resistance of the sensor unit after adsorption of the water molecules from the exhaled breathing air corresponds to the peak flow rate of exhalations from healthy lung;

activating only two LEDs when resistance of the sensor unit after adsorption of the water molecules from the exhaled breathing air corresponds to the peak flow rate of exhalations from lung in condition of COPD;

activate only one LED when resistance of the sensor unit after adsorption of the water molecules from the exhaled breathing air corresponds to the peak flow rate of exhalations from lung seeking emergency medical attention.

According to another aspect, the present Lung condition monitoring device comprises a voltage regulator connected to the power source to maintain the stable output voltage to all components of the device.

According to another aspect, the present Lung condition monitoring device comprises a wireless communication interface for enabling wireless data exchange connectivity between the Lung condition monitoring device and any commercially available mobile phone device having cooperative wireless communication interface.

According to another aspect, an open standard mobile application is developed for the mobile phones operating system and integrated with the present Lung condition monitoring device with the wireless communication interface which enables monitoring of the lung function on the display panel of the mobile phone through wireless data exchange.

BRIEF DESCRIPTION OF THE ACCOMPANYING DRAWINGS

FIG. 5 (A) shows the step by step adsorption and desorption processes of the sensing mechanism; (B) and (C) show the FESEM and TEM images of CdS sensor and synthesized nanoparticles, respectively; (D) shows the humidity sensor arrangement with magnified heating element associated with the present Lung condition monitoring device; (E) illustrates variation of ΔR value of the humidity sensor and recovery time ($t_{rec}$) with the heating element temperature associated with the present Lung condition monitoring device.

DETAILED DESCRIPTION OF THE INVENTION WITH REFERENCE TO THE ACCOMPANYING DRAWINGS

As stated hereinbefore, the present invention discloses a portable Lung condition monitoring device configured for performing ultrafast detection of humidity level in exhaled air while breathing out for checking the fitness of the lungs.

The present Lung condition monitoring device operates as a point-of care testing gadget or device for monitoring condition of the lung and advantageously quantifies the humidity level of exhaled air in order to detect the change in humidity level once user blows the exhaled air through said Lung condition monitoring device.

The relative humidity of the exhaled air from the human lungs is about 95 -100%, which is much larger than the relative humidity of ambient air at room temperature and pressure. Thus, when a human forcibly exhales air on the present Lung condition monitoring device, the change in the humidity level changes electrical resistance across humidity sensor unit of the Lung condition monitoring device. The maximum change in the resistance across the humidity sensor unit can be correlated with the peak flow rate of exhalations from the lungs for detecting lung status and many other health parameters.

The present Lung condition monitoring device comprises said humidity sensing unit having nanoparticle based humidity sensor, heating arrangement having at least one heating element cooperative with the humidity sensor, a mouthpiece and a real time monitoring unit.

Figure 1A:
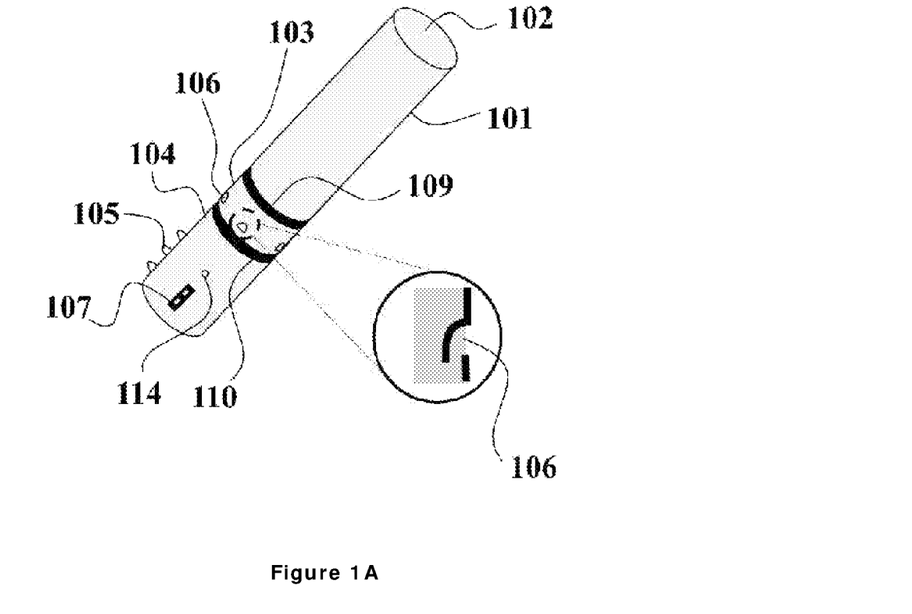
FIG. 1A shows an isometric view of Lung condition monitoring device in accordance to a preferred embodiment of the present invention.
Figure 1B:
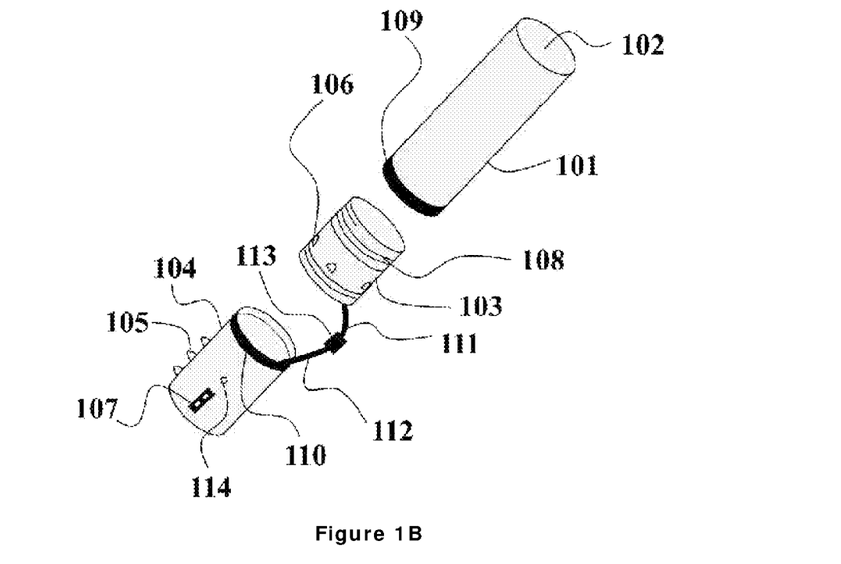
FIG. 1B shows exploded view of the preferred Lung condition monitoring device embodiment.

Reference is first invited from the accompanying FIGS. 1A and 1B which illustrate a preferred embodiment of the present Lung condition monitoring device. As shown in the referred figures, the mouthpiece 101 includes an open area 102 on its proximal end which is used to receive the exhaled breathing air from the user. Distal end of the mouth-piece 101 is attached with threaded portion 108 of the subsequent humidity sensor unit 103. One or more holes 106 are provided on the humidity sensor unit 103 to operate as outlets of the exhaled breathing air in four sides of the humidity sensor unit 103. The inset of the FIG. 1A shows the vertical cross sectional part of outlet holes 106.

The humidity sensor unit 103 is operatively connected to the real-time monitoring unit 104. The real-time monitoring unit comprises plurality of lighting source such as LEDs 105 for indicating status of the lung. The connecting wire 111 from the humidity sensor unit 103 and the connecting wire 112 from the real-time monitoring unit 104 are connected by a connector 113.

In a preferred embodiment, an ON-OFF switch 107 and an ON-OFF indicator LED 114 provided on the real-time monitoring unit 104. Housing of the real-time monitoring unit 104 and the mouthpiece 101 are normally made from plastic or polycarbonate material and preferably includes an O shaped metallic support ring 109 and 110 to protect the housing from cracking and damage.

Figure 2:
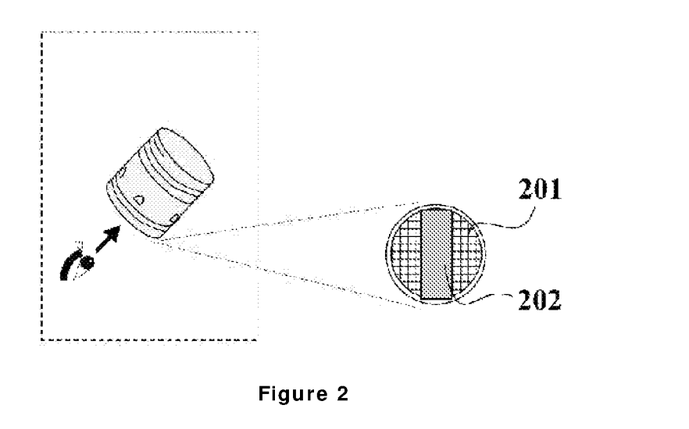
FIG. 2 shows bottom view of humidity sensor unit's exterior associated with the present Lung condition monitoring device.

Reference is next invited from the accompanying FIG. 2 which shows bottom view of the housing of the humidity sensor unit 103. As shown in the figures, the humidity sensor unit's housing includes an opening slot 201 that allows the exhaled air to flow out of the mouthpiece and sensor supporting structure 202 which helps in holding the humidity sensors in the humidity sensor unit housing.

Figure 3:
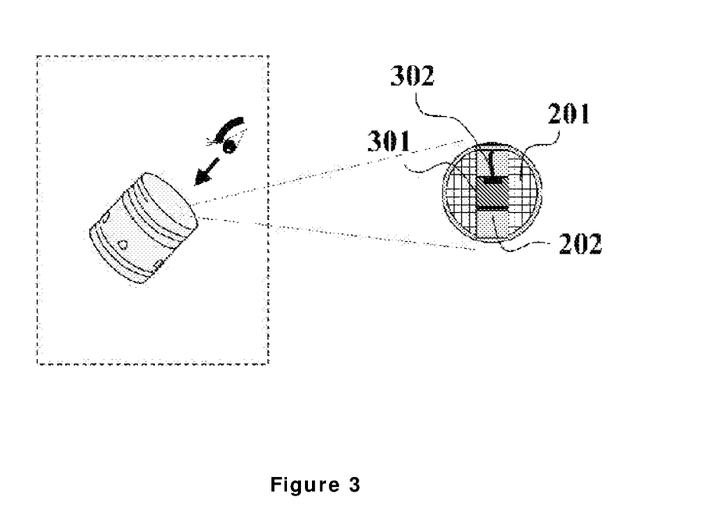
FIG. 3 shows top view of the interior part of the humidity sensor unit.

The accompanying FIG. 3 shows top view of the interior part of the humidity sensor unit 103. The numeral 301 refers to the arrangement of the humidity sensors in the humidity sensor unit 103. The numeral 302 refers to sensor cable which connects the humidity sensors to a control assembly.

Figure 4:
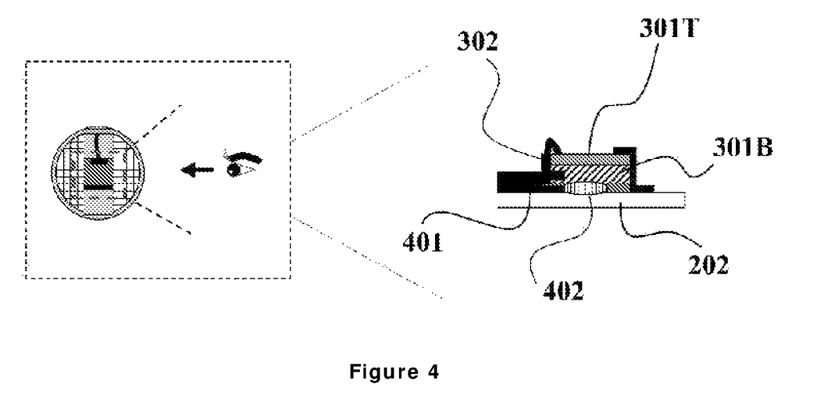
FIG. 4 shows the side view of the humidity sensor unit from the bottom side.

Reference is next invited from the accompanying FIG. 4 which shows side view of the sensor arrangement (301) from the right side of FIG. 3. As shown in the figures, the humidity sensors 301T are arranged over the heating element 301B on the sensor supporting structure 202. A thermistor 402 is provided between the sensor supporting structure 202 and the heating element 301B. In the accompanying figure, the number 302 and 401 are the connector cables of the humidity sensor unit and the heating element respectively.

The nanoparticle based humidity sensors 301T of the humidity sensor unit 103 preferably include one or more films of porous CdS nanoparticles which are not only capable of rapid adsorption of water molecules under the sudden exposure of water vapor, but also can desorb water immediately upon heating.

Reference is next invited from the accompanying FIGS. 5(A)-(D) which show the characterization of the CdS nanoparticles and arrangement of the CdS nanoparticle based humidity sensors including the mechanism of adsorption and desorption of the water molecules from the exhaled air on the CdS nanoparticles and the FESEM and TEM characterization of the deposited CdS nanoparticles.

Figure 5A:
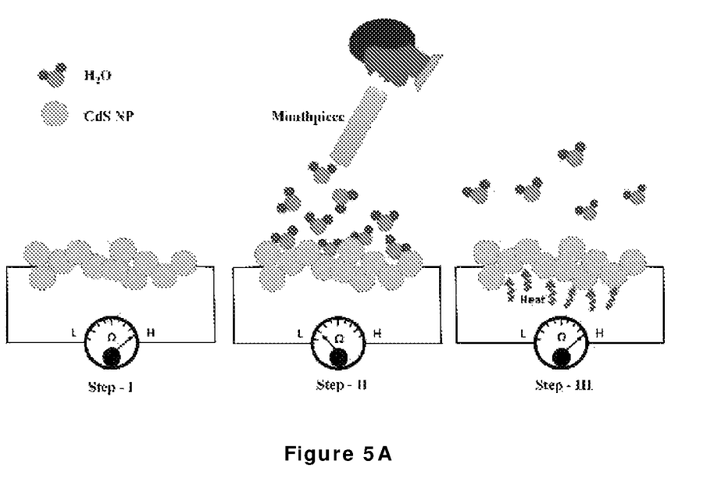
Figure 5B:
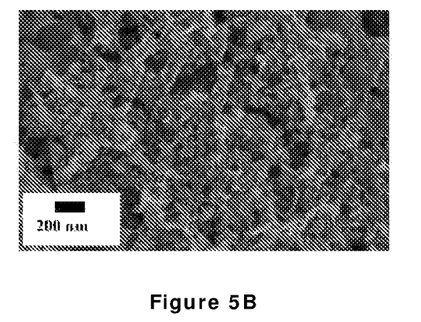
Figure 5C:
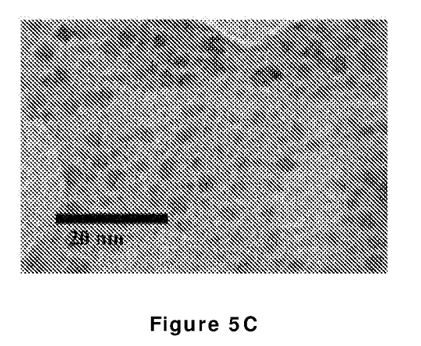

The accompanying FIG. 5(A) schematically shows the step by step process of adsorption of water molecules on the CdS nanoparticles, the reduction in the electrical resistance thereof, and then desorption of the water molecules through heating. The accompanying FIGS. 5(B) and 5(C) show the FESEM and TEM images of the CdS nanoparticle sensor and synthesized nanoparticles, respectively.

Figure 5D:
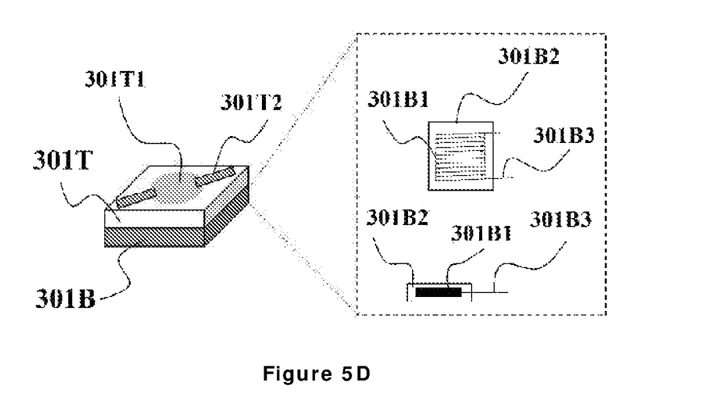

The FIG. 5(D) shows the detailed illustration of the CdS nanoparticle based humidity sensors and the heating element. The heating element 301B is further magnified and top view (upper image in the dotted box) and side view (lower image in the dotted box) are shown.

The heating element includes metallic wire of a coil form 301B1 which is embedded in a polymer (preferably polydimethylsiloxane (PDMS)) matrix 301B2. Two electrodes 301B3 are provided for connecting a power source with the coil 301B1 to operate the heating element and generate heat.

As shown in the figure, the CdS nanoparticle sensors 301T includes sensor paper 301T1 substrate having the CdS nanoparticles and silver electrodes 301T2.

In the present invention, the CdS nanoparticles are first synthesized by using chemical precipitation technique [refer to, Qi et. al., Nano Letters, 2001, 1, 61-65] wherein $CdCl_2$ is used as the source of $Cd^{2+}$ ions and $Na_2S$, $9H_2O$ is used as the source of $S^{2-}$ ions. Methanol acted as a capping agent.

In the beginning of the synthesis a 20 ml of 0.1M NaOH solution is prepared which is then slowly added to 2.5 ml of methanol that acted as capping agent. This prepared solution is then sonicated for 1 hr in ultra-sonication bath. Freshly prepared $Na_2S$ solution is then added to the aforementioned solution drop by drop with vigorous stirring, which turned the colorless solution to a yellowish solution. Prepared CdS nanoparticles are accumulated at the bottom of the container and 50 µl CdS nanoparticle is dropped on the filter paper i.e. the sensor paper substrate (Whatman cat no. 1001 125 grade 1) of dimension 1 cm×1 cm using micropipette. The sample is then kept for 12 h to get dried. Then silver paste is used to make the silver electrodes and the prepared sample is kept again for 24 h in order to get dried.

In the present invention, the paper used for fabrication of the sensor is pretreated with Au nanoparticle solution for embedding the Au nanoparticle within the paper substrate, wherein the paper is kept inside Au nanoparticle solution for 2 h and then dried in hot-air oven. Pretreatment of the paper substrate increase the thermal conductivity of the paper substrate as the embedded Au nanoparticles played important role in conduction of heat. Pretreatment of the paper with Au nanoparticle solution helped in improving the recovery time with less temperature requirement.

In a preferred embodiment, the heating element is fabricated by using Cu wire of diameter 180 µm. A long copper wire is coiled in a 1 cm square area and made a square having 80 turns of copper wire. This is then fixed in an adhesive paper substrate to keep the structure intact. Then the CdS humidity sensor is integrated with the heating element by placing it top of the heating element and connecting it to the connector.

Figure 5E:
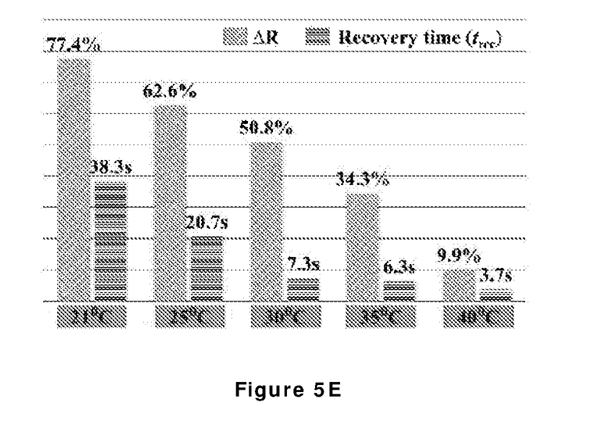

The accompanying FIG. 5(E) depicts the typical variations in the change in the resistance ($\Delta R$) and recovery time ($t_{rec}$) with the temperature of the heating element. The NTC thermistor ($R_t$) which is placed below the heating element, senses the temperature of the heating element and acts as a negative feedback to control temperature. As shown in the FIG. 5(E), the recovery time of the nanoparticle sensor decreases rapidly with increase in temperature, which in turn is clear indication of high rate of desorption of water molecule from the nanoparticle sensor surface.

Since the exhaled breathing air issuing out of a human lung is exceedingly humid, when the user exhales air on the mouthpiece 101, the immediate vicinity of the CdS nanoparticle humidity sensors 301T of the humidity sensor unit 103 becomes crowded with a large number of water molecules. Consequently, a part of these water molecules are adsorbed by the porous CdS nanoparticles, as schematically shown in the FIG. 5(A). The adsorption process on the surface of the porous CdS nanoparticles becomes rapid owing to the forced exhalation, which causes a very sharp change in electrical resistance in the humidity sensor unit 103 during the process of forced exhalation. The change of electrical resistance can be employed to quantify the peak flow of exhalation.

Experiments suggest that when RH of the surroundings are relatively low (~5%), a Langmuir monolayer of water molecules on the surface of the CdS nanoparticles having active OH groups may not change the electrical resistance significantly [refer to, Demir et al., Ind. Eng. Chem. Res. 2011, 50, 5606]. However, at higher RH values (>60%) condensation of water molecules on CdS surface due to multilayer physical adsorption lead to a significant decrease in the electrical resistance. In such a scenario, the reduction in the electrical resistance can be attributed to the enhancement in the ionic conduction, which happened because of the production of ionic hydroxyl groups from the adsorbed water molecules when the electric field applied across the CdS surface. Thus, the CdS nanoparticle based humidity sensors employed in the humidity sensor unit of the present lung status testing device show a rapid reduction in the electrical resistance while the forced exhalation takes place. However, the rate of desorption of the water molecule is rather slow because of the higher level of RH in the surroundings. In order to expedite the rate of desorption and reduce the time for recovery of the humidity sensors, the heating element is used to increase temperature of the CdS nanoparticle humidity sensors which rapidly enhance rate of desorption of water molecule from the nanoparticle sensor surface.

Figure 6:
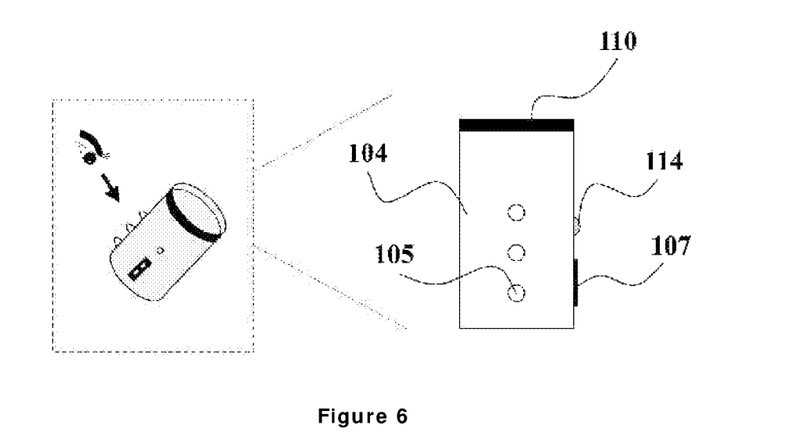
FIG. 6 shows isometric view of real-time monitoring unit associated with the present Lung condition monitoring device.
Figure 7:
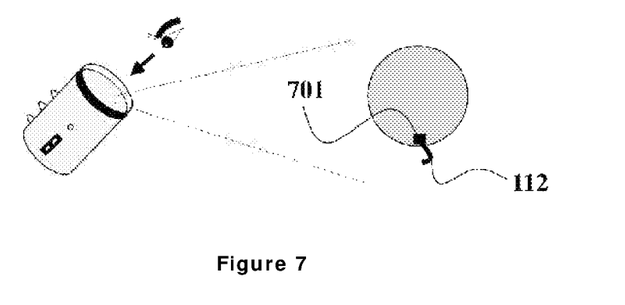
FIG. 7 shows top view of the real time monitoring unit associated with the present Lung condition monitoring device.
Figure 8:
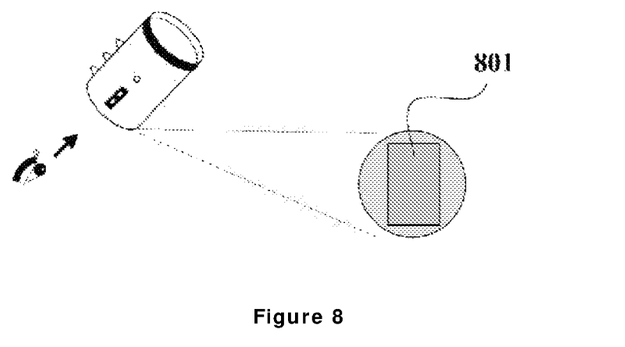
FIG. 8 shows back side view of the real time monitoring unit associated with the present Lung condition monitoring device.

Reference is next invited from the accompanying FIGS. 6-8 which show the assembly of the real time monitoring unit 104. The real time monitoring unit 104 is embodiment of a small cabinet made of plastic which houses the control assembly and the power source.

The accompanying FIG. 6-8 illustrates different parts of this real time monitoring unit 104 and their assemblage with the present lung testing device. The number 701 is the opening from where the connector cable 112 of the control assembly comes out and the number 801 is the space for accommodating the power source or battery and the control assembly.

The real time monitoring unit 104 is connected to the humidity sensor unit 103 as illustrated in the FIG. 1. When the user exhales forcefully in the mouth-piece 101 the humidity change is detected by the humidity sensors of the humidity sensor unit resulting generation of an equivalent electrical signal, which travels to the monitoring unit 104 via the connector route 111-113-112. The generated electrical signal which is equivalent to the humidity change as detected by the humidity sensor unit is correlated to the change in the resistance in the humidity sensor and it is measured in the control assembly based on which one or more indicator LEDs 105 of the real time monitoring unit 104 (LEDs $L_R$, $L_Y$ and $L_G$) can be turned ON by involving a resistive network according to the detected level of the humidity. For healthy breathing, all the LEDs (green, yellow, and red) are expected to glow. When the green LED is off and red and yellow glow, then the user may have an onset condition of COPD. For red glowing the device after forced exhalation may seek emergency medical attention.

Figure 9:
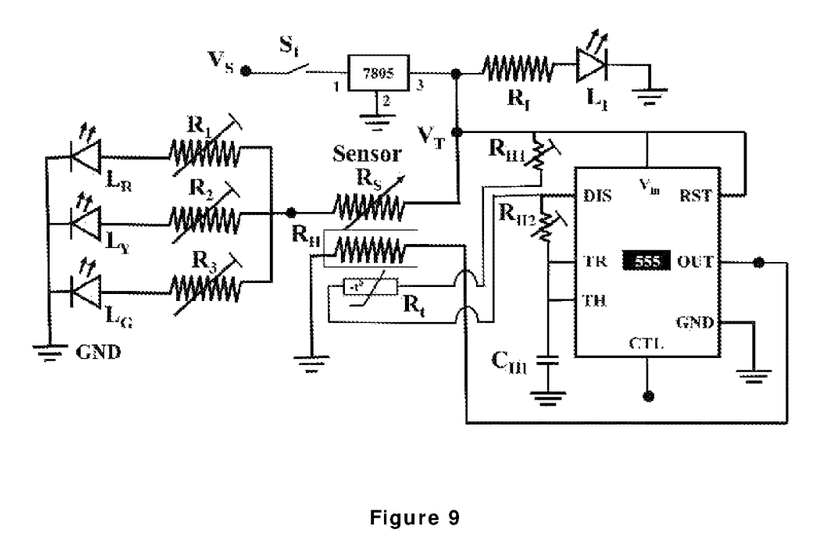
FIG. 9 shows circuit representation of control assembly associated with the present Lung condition monitoring device.
Figure 10A:
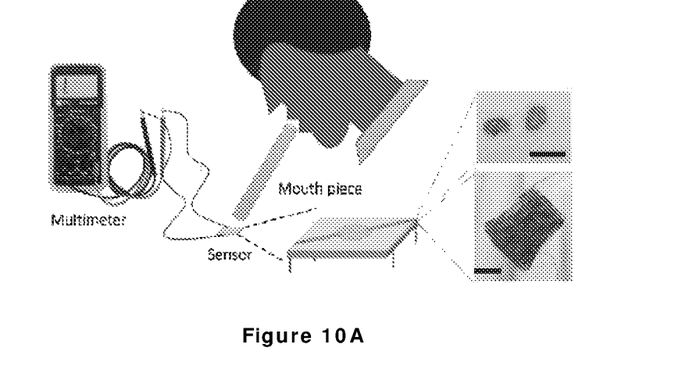
FIG. 10(A) schematically shows the experimental set up composed of the components, namely, mouth piece, sensor, heating arrangement, and multi-meter to measure the peak flow of exhalation. The insets also show the real images of humidity sensor and heating element where the scale bars are of 5 mm; (B) and (C) show the real image of the device prototype after integration; (D) shows the repetition of the change in resistance for three cycles of breathing and a control experiment with dry $N_2$ gas which is introduced to the humidity sensor in a pulse mode; (E) shows the change in resistance due to different peak flow rate of exhaled air; (F) shows the comparison of peak results between a commercial device (JSB N02 Peak Flow Meter) and present device for five different volunteer.
Figure 10B:
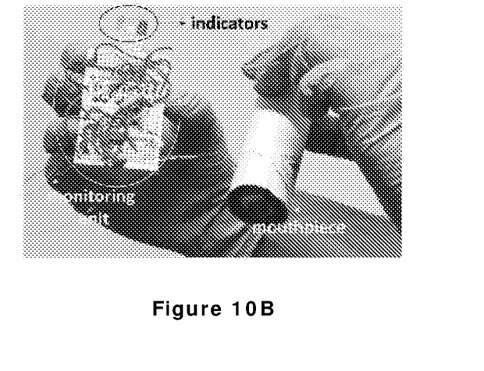
Figure 10C:
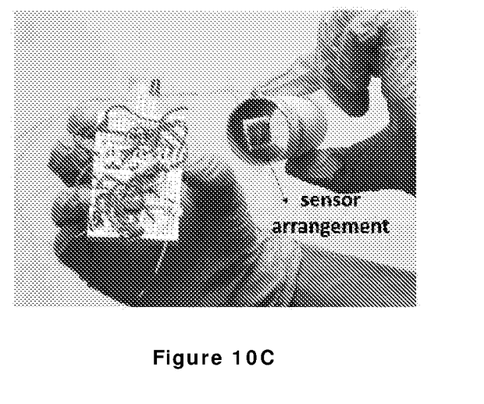

Reference is next invited from the accompanying FIG. 9 which illustrates the control assembly of the Lung condition monitoring device installed in the monitoring unit 104. The control assembly can be divided in three different parts, namely, sensor unit control module, heating element control module, and indicator LED control module.

As shown in the referred figure, the heating element control module which is associated with the heating element (RH) 301B is situated in right side of the sensor unit control module. The heating element control module includes a square pulse generator that helps in maintaining the heating element temperature. The display LED control module which displays the sensor response through the indicator LEDs is situated in the left side of the of the sensor unit control module.

Three indicator LEDs 105 ($L_R$, $L_Y$ and $L_G$) are connected to the sensor ($R_S$) via three variable resistances ($R_1$, $R_2$ and $R_3$) of the indicator LED control module, as shown in the FIG. 9. The frequency and duty cycle is maintained by adjusting the values of $R_{H1}$, $R_{H2}$, and $C_{H1}$. A voltage regulator 7805 is connected to the power source to maintain the output voltage as 5 V. The S1 indicates the ON-OFF switch 107 and $L_1$ is the ON-OFF indicator LED 114. The NTC thermistor $R_t$ 402 is connected in series to the resistor $R_{H1}$ as a feedback to maintain the temperature of the heating element $R_H$ 301B. Here $V_S$, $V_T$, and GND denote the supply voltage, terminal voltage, and ground terminal, respectively.

Reference is next invited from the accompanying FIG. 10A-10F which schematically shows the typical components of the present lung status testing device such as mouth-piece, sensor unit, heating element, and sensor arrangement.

The insets also show the real images of humidity sensor unit and heating element. The accompanying figures (B) and (C) show the real image of the device prototype after integration. The figure (D) shows the repetition of the change in resistance for three cycles of breathing.

In the present Lung condition monitoring device, the peak flow rate ($F_R$) of exhaled air is measured, which is the maximum speed of exhalation of a person and a potential indicator of the degree of obstruction in the airways of the bronchi. Dependence of the change in the resistance of the nanoparticle humidity sensor due to adsorption of water in the nanoparticle sensor surface with the peak flow rate is shown in the accompanying FIG. 10E. The higher value of $F_R$ indicates healthy lungs whereas lower values indicate the diseased state of the lungs. The scale of the peak flow rate ($F_R$) of exhaled air is generally divided into three different zones like green, yellow, and red depending upon the severity where red zone indicates a medical emergency and green zone indicates normal or healthy lungs.

The accompanying FIG. 10F shows the comparison of peak results between a commercial device (JSB N02 Peak Flow Meter) and present Lung condition monitoring device for five different volunteers.

As stated herein before, the indicator LED control module of the present device can activate one or more of the indicator LEDs depending on the change in the electrical resistance of the sensor unit and correlating the same with the peak flow rate of exhalations from lung, wherein the peak flow rate of exhalations from the lung is linearly vary with the change in the resistance of the nanoparticle sensor due to the adsorption of the water molecules from the exhaled breathing air during forced exhalation. In an embodiment of the present Lung condition monitoring device, wherein the indicator LED control module is configured to activate any one or more of three indicator LEDs for indicating status of the lung includes the resistive network adapted to drive current through the LEDs for activating all the LEDs when resistance of the sensor unit after adsorption of the water molecules from the exhaled breathing air corresponds to the peak flow rate of exhalations from healthy lung or activating only two LEDs when resistance of the sensor unit after adsorption of the water molecules from the exhaled breathing air corresponds to the peak flow rate of exhalations from lung in condition of COPD or activate only one LED when resistance of the sensor unit after adsorption of the water molecules from the exhaled breathing air corresponds to the peak flow rate of exhalations from lung seeking emergency medical attention.

Figure 11A:
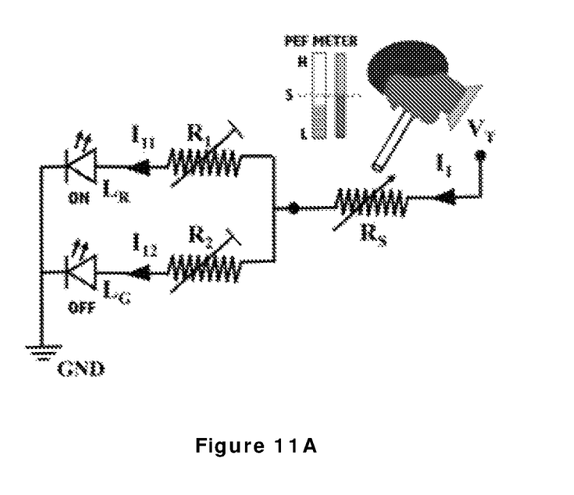
FIGS. 11(A) and (B) shows description and illustration of detection circuit of the control assembly.
Figure 11B:
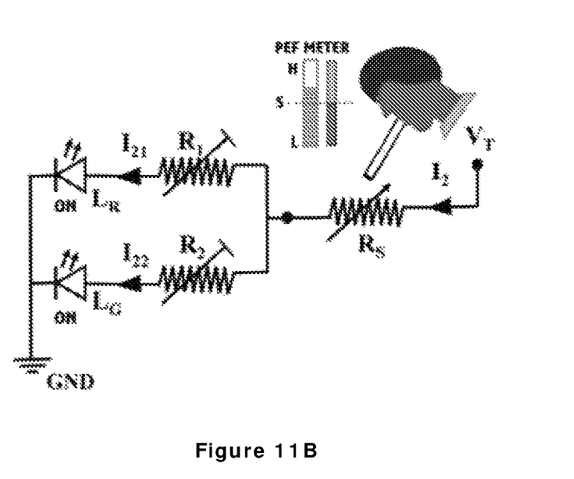

To illustrate the above selective driving of the current through the LEDs, reference is now invited from the accompanying FIGS. 11(A) and 11(B). As mentioned previously, the change in the resistance of the nanoparticle sensor ($\Delta R$) with the peak flow of the exhaled air ($F_R$), as illustrated in the FIG. 10(E). For the sake of simplicity, it is assumed that the device may illuminate red LED ($L_R$) for deteriorating condition and green LED ($L_G$) for a healthy condition of the lungs.

The FIGS. 11(A) and 11(B) show these two different situations for the illumination of red and green LEDs. In case of FIG. 11(A), the $F_R$ is below the desired level (S) as shown in the imaginary scale, which is made for better understanding. In contrast, FIG. 11(B) shows the situation where $F_R$ is above the safety level (S). It may be noted here that the $\Delta R$ is more in case of FIG. 11(B) than that of FIG. 11(A).

To illustrate operation of the present device, it is assumed that $R_{SA}$=10 k$\Omega$, which is the resistance value of $R_S$ in case of FIG. 11(A) and $R_{SB}$=5 k$\Omega$, which is the resistance value of $R_S$ in case of FIG. 11(B). Say, the minimum current to illuminate an LED is 0.3 mA and the circuit as shown in FIG. 11(A) is designed in such a manner that when the $F_R$ is below safety level, then red LED $L_R$ glows while the green LED $L_G$ remains turned off. In comparison, when $F_R$ is above safety level, both red and green LEDs glow. To achieve this, the resistances are tuned to have, $R_1$=5 k$\Omega$ and $R_2$=10 k$\Omega$ for a terminal voltage $V_T$=9 V. It is assumed that the LEDs have negligible internal resistance in order to reduce the complexity. From circuit theory, the total current through $R_{SA}$ when $F_R$ is below the safety level can be given by, $$I_1 = \frac{V_T}{\frac{R_1 R_2}{R_1 + R_2} + R_{SA}}$$

Similarly, when $F_R$ is above safety level, the current, $$I_2 = \frac{V_T}{\frac{R_1 R_2}{R_1 + R_2} + R_{SB}}$$

When, $F_R$ is below safety level, the total current is $I_1$ and in this condition the current through $R_1$ is, $$I_{11} = I_1 \times \left(\frac{R_2}{R_1 + R_2}\right)$$

and the current through $R_2$ is, $$I_{12} = I_1 \times \left(\frac{R_1}{R_1 + R_2}\right).$$

If one put all the values, then $I_1 = 0.675$ mA, $I_{11}=0.45$ mA and $I_{12}=0.225$ mA, which confirms that in this case only the red LED ($L_R$) is turned on to indicate the necessity of medical assistance required. In contrast, if the $F_R$ is above safety level, then $I_2=1.08$ mA, $I_{21}=0.72$ mA and $I_{22}=0.36$ mA, which ensures both the green and red LEDs ($L_G$ and $L_R$) are turned on to confirm fitness of the Lungs.

Figure 12:
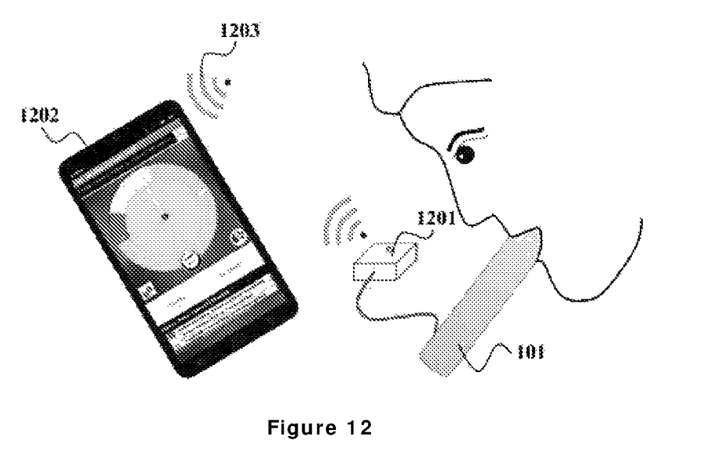
FIG. 12 shows Bluetooth interfacing of the present Lung condition monitoring device to peripheral computing device.

This device can also be operated using a peripheral computing device such as smart mobile phone with an open standard 'Android' operating system in which an 'Android' application is developed specific to the Lung condition monitoring device. The FIG. 12 shows the mobile interfacing schematically where one Bluetooth module 1201 is connected to the Lung condition monitoring device. This Bluetooth module connects the physical device to an Android mobile application 1202 which receives data from the humidity sensor and displays on the mobile screen. This mobile connectivity feature increases the portability, data monitoring, and user friendliness of the device. Moreover, the big time data can be stored and analyzed using the mobile interface.

Although the above embodiments of the invention have been illustrated as a unique Lung condition monitoring device which advantageously detect condition of the lung in real time and operate as point-of care testing gadgets or devices for checking fitness of the lungs of a person, the present device, can also be engineered even for detecting humidity level in the air. At its present state, the sensor gives a sharp and rapid response for the forcibly flowing highly humid air such as human exhaled air. However, it has the capability to detect the humidity level of air, and to remove the effect of ambient humidity, the heating element is introduced which confirms that the ambient water molecules cannot effect the sensor response during measuring the lung health.

Those skilled in the art will recognize, however, that the embodiments of the invention described herein are only examples provided for the purpose of describing the advancement only and that they are not the only embodiments of the Lung condition monitoring device which can be developed involving the advancement. Thus other changes and modifications known to those of ordinary skill are intended to be included within the scope of the present invention.

We claim:

1. A lung condition monitoring device comprising:
   a mouthpiece for forcibly exhaling air therethrough;
   a humidity sensor configured to output variable electrical resistance based on a level of adsorption of water molecules thereon of humidity of the exhaled air;
   a real time monitoring unit operatively connected to said humidity sensor and configured for correlating a change in humidity level and related variation in the electrical resistance due to exhalation to a peak flow rate of the exhaled air for monitoring lung condition; and
   a heating element for rapid desorption of the water molecules from the humidity sensor and recovery of the humidity sensor for subsequent detection of the humidity level.

2. The lung condition monitoring device as claimed in claim 1, further comprising a humidity sensor unit exposed to a rapid decrease in the electrical resistance of the humidity sensor due to the adsorption of the water molecules from the exhaled breathing air during forced exhalation; wherein:
   said mouthpiece includes an open area to receive exhaled breathing air from a user, wherein said mouthpiece, at a remote end, is operatively connected to said humidity sensor in the humidity sensor unit;
   said heating element cooperates with said humidity sensor to increase temperature of the humidity sensor post adsorption of the water molecules for rapid desorption of the water molecule from the humidity sensor and recovery of the humidity sensor for subsequent detection of the humidity level; and
   said real time monitoring unit is configured to detect a lung condition and lung function parameters by detecting a maximum change in the electrical resistance across the humidity sensor and correlating the same with the peak flow rate of exhalations from lung.

3. The lung condition monitoring device as claimed in claim 2, wherein the humidity sensor unit comprises:
   at least one opening slot to allows the exhaled breathing air to flow in;
   one or more holes on a sidewall of humidity sensor unit's housing to operate as outlets of the air from the humidity sensor unit; and
   sensor supporting structure to hold the humidity sensor in the humidity sensor unit.

4. The lung condition monitoring device as claimed in claim 3, wherein the humidity sensor includes:
   one or more films of porous cadmium sulfide (CdS) nanoparticles, each of said films of porous CdS nanoparticles comprising
   i. a thermally conductive paper substrate having gold (Au) nanoparticles embedded thereon, and
   ii. the porous CdS nanoparticles on said Au nanoparticles embedded thermally conductive paper substrate to constitute a nanoparticle surface for rapid adsorption of the water molecules; and
   silver electrodes for operatively connecting said nanoparticle surfaces with the real time monitoring unit.

5. The lung condition monitoring device as claimed in claim 4, wherein the heating element is placed between the humidity sensors and the sensor supporting structure.

6. The lung condition monitoring device as claimed in claim 5, wherein the heating element comprises:
   a metallic wire in coil form embedded in a polymer matrix or substrate; and
   two electrodes for connecting a power source with the coil to operate the heating element and generate heat.

7. The lung condition monitoring device as claimed in claim 5, further comprising a thermistor positioned between the sensor supporting structure and the heating element to sense temperature of the heating element and act as a negative feedback to control the temperature.

8. The lung condition monitoring device as claimed in claim 6, wherein the heating element includes copper wire of diameter 180 μm coiled in a 1 centimeter square area having 80 turns fixed in an adhesive paper substrate to keep the structure intact.

9. The lung condition monitoring device as claimed in claim 2, wherein the real time monitoring unit includes:
   a small cabinet for housing a control assembly and the power source;
   a plurality of indicator LEDs on housing of the real time monitoring unit for indicating status of the lung; and a power switch operatively connected with the power source to activate/deactivate the device and ON-OFF indicator LED to display activation of the device.

10. The lung condition monitoring device as claimed in claim 9, wherein the control assembly includes:
   a heating element control module comprising a square pulse generator to operate and maintain the heating element's temperature;
   a sensor unit control module having said humidity sensor and configured to connect the humidity sensor with the indicator LED control module via associated resistive network; and
   an indicator LED control module having a resistive network operatively connecting the indicator LEDs with the humidity sensor to activate one or more of the indicator LEDs depending on the condition of the lung of the user.

11. The lung condition monitoring device as claimed in claim 10,
   wherein the indicator LED control module is configured to activate one or more of the indicator LEDs depending on the change in the electrical resistance of the humidity sensor and correlating the same with the peak flow rate of exhalations from lung;
   wherein the peak flow rate of exhalations from the lung is an indicator of degree of obstruction in airways of bronchi and linearly vary with the change in the electrical resistance of the humidity sensor due to the adsorption of the water molecules from the exhaled breathing air during forced exhalation; and
   wherein higher value of the peak flow rate of exhalations indicates healthy lungs and lower values indicate the diseased state of the lungs.

12. The lung condition monitoring device as claimed in claim 11, wherein the indicator LED control module is configured to activate any one or more of three indicator LEDs for indicating status of the lung and includes the resistive network adapted to drive current through the LEDs for
   activating all the LEDs when resistance of the sensor unit after adsorption of the water molecules from the exhaled breathing air corresponds to the peak flow rate of exhalations from a healthy lung;
   activating only two LEDs when resistance of the sensor unit after adsorption of the water molecules from the exhaled breathing air corresponds to the peak flow rate of exhalations from a lung in condition of COPD; and
   activating only one LED when resistance of the sensor unit after adsorption of the water molecules from the exhaled breathing air corresponds to the peak flow rate of exhalations from a lung in need of emergency medical attention.

13. The lung condition monitoring device as claimed in claim 6, further comprising a voltage regulator connected to the power source to maintain the stable output voltage to all components of the device.

14. The lung condition monitoring device as claimed in claim 1, further comprising a wireless communication interface having wireless data exchange connectivity with a peripheral computing device to facilitate wireless data transfer from the humidity sensor to the peripheral computing deivce and display the same on the peripheral computing device screen;
   wherein the connected periphal computing device facilitates storage and analysis of big time data for prognosis, diagnosis, and therapeutic purposes and also increases portability, data monitoring, and user friendliness of the device.

15. The lung condition monitoring device as claimed in the claim 14, further including an open standard mobile application for the peripheral computing device operating system configured for integrating with the present lung condition monitoring device and the wireless communication interface to enable monitoring of the lung function on the screen of the peripheral computing device through wireless data exchange.

* * * * *